United States Patent
Simonian et al.

(10) Patent No.: US 7,345,806 B2
(45) Date of Patent: Mar. 18, 2008

(54) METHOD AND APPARATUS FOR CHARACTERIZING MICROELECTROMECHANICAL DEVICES ON WAFERS

(75) Inventors: Dmitri Simonian, Sunnyvale, CA (US); Casey Feinstein, San Francisco, CA (US)

(73) Assignee: Texas Instruments Incorporated, Dallas, TX (US)

( * ) Notice: Subject to any disclaimer, the term of this patent is extended or adjusted under 35 U.S.C. 154(b) by 269 days.

(21) Appl. No.: 10/875,555

(22) Filed: Jun. 23, 2004

(65) Prior Publication Data

US 2005/0286105 A1  Dec. 29, 2005

(51) Int. Cl.
*G02B 26/00* (2006.01)
*H01J 5/16* (2006.01)
(52) U.S. Cl. .............. 359/291; 359/290; 250/216
(58) Field of Classification Search .......... 356/72–73, 356/121–122; 359/290–295, 237, 224; 250/492.2, 250/492.3; 219/121.69
See application file for complete search history.

(56) References Cited

U.S. PATENT DOCUMENTS

| | | | | |
|---|---|---|---|---|
| 5,629,790 A * | 5/1997 | Neukermans et al. | ........ | 359/198 |
| 5,661,591 A * | 8/1997 | Lin et al. | ........ | 359/290 |
| 5,796,508 A * | 8/1998 | Suzuki | ........ | 359/224 |
| 5,870,176 A * | 2/1999 | Sweatt et al. | ........ | 355/53 |
| 6,052,197 A * | 4/2000 | Drake | ........ | 356/445 |
| 6,088,474 A | 7/2000 | Dudasko et al. | | |
| 6,348,907 B1 * | 2/2002 | Wood | ........ | 345/84 |
| 6,515,278 B2 * | 2/2003 | Wine et al. | ........ | 250/234 |
| 6,566,627 B2 * | 5/2003 | Brandinger et al. | ... | 219/121.69 |
| 6,707,351 B2 * | 3/2004 | Gorrell | ........ | 333/188 |
| 6,747,783 B1 * | 6/2004 | Sandstrom | ........ | 359/290 |
| 6,751,370 B2 * | 6/2004 | Avakian et al. | ........ | 385/18 |
| 6,798,560 B2 * | 9/2004 | Aubuchon | ........ | 359/291 |
| 6,922,233 B2 * | 7/2005 | Riza | ........ | 356/121 |
| 6,987,599 B2 * | 1/2006 | Sandstrom | ........ | 359/290 |
| 6,998,219 B2 * | 2/2006 | Fries | ........ | 430/311 |
| 6,998,851 B2 * | 2/2006 | van Spengen | ........ | 324/523 |
| 7,019,376 B2 * | 3/2006 | Patel et al. | ........ | 257/436 |
| 7,034,984 B2 * | 4/2006 | Pan et al. | ........ | 359/291 |
| 2003/0218753 A1 | 11/2003 | Reuter | | |
| 2003/0223084 A1 | 12/2003 | Mehri et al. | | |
| 2004/0042000 A1 | 3/2004 | Mehri et al. | | |

OTHER PUBLICATIONS

Henry Chu, et al., "DMD superstructure Characterizations", Jul.-Sep. 1998, pp. 75-86.
W.N. Sharpe, et al. "Tensile testing of MEMS materials-recent progress". Journal of Materials Science 38 (2003), pp. 4075-4079.
T.E. Buchheit, et al., "Micromechanical testing of MEMS materials", Journal of Materials Science 38 (2003), pp. 4081-4086.
S.M. Allameh, et al., "An introduction to mechanical-properties-related issues in MEMS structures", Journal of Materials Science 38 (2003), pp. 4115-4123.
S.M. Allameh, et al., Surface topography evolution and fatigue fracture of polysilicon, Journal of Materials Science 38 (2003), pp. 4145-4155.
Ken Gall, et al., "Thermomechanical response of bare and $Al_2O_3$—nanocoated Au/Si bilayer beams for micromechanical systems", J. Mater. Res., vol. 18, No. 7, Jul. 2003, pp. 1575-1587.

* cited by examiner

*Primary Examiner*—Sang H. Nguyen
(74) *Attorney, Agent, or Firm*—Wade James Brady, III; Frederick J. Telecky, Jr.

(57) ABSTRACT

The invention provides a method and apparatus for evaluating the quality of microelectromechanical devices having deformable and deflectable members using resonation techniques. Specifically, product quality characterized in terms of uniformity of the deformable and deflectable elements is inspected with an optical resonance mapping mechanism on a wafer-level.

32 Claims, 8 Drawing Sheets

US 7,345,806 B2

METHOD AND APPARATUS FOR CHARACTERIZING MICROELECTROMECHANICAL DEVICES ON WAFERS

TECHNICAL FIELD OF THE INVENTION

The present invention relates to the field of microelectromechanical devices, and more particularly to methods and apparatus for characterizing microelectromechanical devices on wafers after fabrication.

BACKGROUND OF THE INVENTION

Microelectromechanical (MEMS) devices have found many applications in basic signal transductions. For example, MEMS-based spatial light modulators are transducers that modulate incident light in a spatial pattern in response to optical or electrical inputs. The incident light may be modulated in phase, intensity, polarization, or direction. This modulation may be accomplished through the use of a variety of materials exhibiting magneto-optic, electro-optic, or elastic properties. Such spatial light modulators have many applications, including optical information processing, display systems, and electrostatic printing.

A microelectromechanical device often contains one or more deformable and/or deflectable members. For example, a typical micromirror-based spatial light modulator consists of an array of deflectable mirror plates that are formed on a substrate with each mirror plate being attached to a deformable hinge. In operation, the mirror plates are individually addressable and deflectable with electrostatic fields so as to modulate incident light. The performance of the spatial light modulator depends upon the coordination of the mirror plates. That is, the successful light modulation depends on the uniformity of the mirror plates and hinges.

For quality assurance purposes, it is certainly required to inspect the functional members of microelectromechanical devices before delivery to customers. The inspection, however, is often preferably to be performed during the fabrication process for many reasons. For example, after completion of the deformable and/or deflectable elements, one or more succeeding processing steps, such as surface treatment, assembly and packaging are often required before the completion of the fabrication process. From at least the cost-effective point of view, inspection of the formed deflectable and/or deformable elements is desired to be conducted before performing the succeeding processing steps. According to the inspection, the fabricated devices not satisfying the predetermined criterion can be discarded, while the fabricated devices satisfying the criterion are saved for further processes.

Therefore, what is desired is a method and apparatus for inspecting fabricated microelectromechanical devices having deflectable and/or deformable members.

SUMMARY OF THE INVENTION

The objects and advantages of the present invention will be obvious, and in part appear hereafter and are accomplished by the present invention that provides a method and apparatus for operating pixels of spatial light modulators in display systems. Such objects of the invention are achieved in the features of the independent claims attached hereto. Preferred embodiments are characterized in the dependent claims. In the claims, only elements denoted by the words "means for" are intended to be interpreted as means plus function claims under 35 U.S.C. §112, the sixth paragraph.

BRIEF DESCRIPTION OF DRAWINGS

While the appended claims set forth the features of the present invention with particularity, the invention, together with its objects and advantages, may be best understood from the following detailed description taken in conjunction with the accompanying drawings of which:

DETAILED DESCRIPTION OF THE EMBODIMENTS

Figure 1:
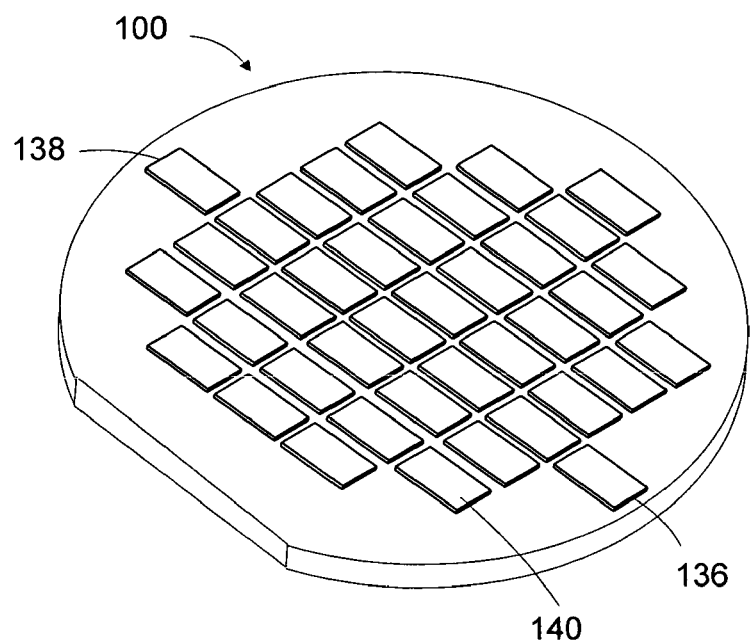
FIG. 1 is a perspective view of a wafer having a plurality of dies, each of which has an array of fabricated micromirrors.

The invention provides a method and apparatus for evaluating the quality of microelectromechanical devices having deformable and/or deflectable members using resonation techniques. Specifically, product quality characterized in terms of uniformity of the deformable and/or deflectable elements is inspected with an optical resonance mapping mechanism on wafer-level.

The wafer may comprise a plurality of dies, each of which comprises a set of functional components with each functional component further comprises one or more freed deflectable and/or deformable elements. The deflectable elements have light reflective surfaces for reflecting incident light. The functional components each may or may not be a fully developed device—that is each functional component can be a portion of a desired device and wait for further process or processes.

In order to inspect the uniformity of the freed elements, an AC voltage having a small amplitude (a disturbing AC voltage) as compared to the voltage necessary to actuate the deflectable elements to a desired operation state (e.g. the ON state) is applied to the deflectable elements. With the applied AC voltage, the deflectable elements oscillate in the vicinity of their equilibrium state (e.g. the natural resting states). When the frequency of the AC voltage is approximately the intrinsic resonance frequency of the deflectable elements, the oscillation amplitudes of the deflectable elements are maximized.

The oscillations and the resonance frequencies can be measured by directing a light beam onto the reflective surfaces of the deflectable elements and measure the intensity of the reflected light beams from the oscillating deflectable elements. From the distribution of the measured resonance frequencies of the deflectable elements across the entire wafer, the uniformity information can be extracted and can be quantitatively and qualitatively analyzed.

Based on the uniformity information, the fabricated (or partially fabricated) devices on the wafer can be saved for further processes when a predetermined quality criterion is satisfied, or can be discarded otherwise. Moreover, the uniformity information can be used for the following processes if desired. In particular, the partially fabricated functional components on the wafer can be arrays of mirror plates and hinges on a glass substrate of micromirror-based spatial light modulators, each further comprising an array of electrodes and circuitry formed on a separate semiconductor wafer. During the fabrication, the micromirror arrays are formed on the glass wafer in the form of a plurality of dies with each die being a micromirror array. The electrodes and circuitry are formed on the semiconductor wafer in the form of a plurality of dies with each die being an array of electrodes and circuitry. The mirror plates and hinges on the glass wafer and the electrodes and circuitry on the semiconductor wafer are fabricated separately, and assembled together afterwards such that the micromirrors of the glass substrate can be individually addressed and actuated by the electrodes on the semiconductor wafer, as set forth in U.S. Pat. No. 6,046,840, to Huibers, issued on Apr. 4, 2000; and U.S. patent application Ser. No. 09/767,632, to True et al, filed on Jan. 22, 2001, Ser. No. 10/005,308, to Patel, filed on Dec. 3, 2001, and P085-US, Ser. No. 10/305,536, to Huibers, filed on Nov. 26, 2002, the subject matter of each being incorporated herein by reference. Before the assembling process, "good" dies (i.e. the dies satisfying the predetermined quality criterion) and "bad" dies (i.e. the dies not satisfying the criterion) on the glass wafer can be identified across the glass wafer according to the uniformity information of the glass wafer. On the semiconductor wafer, the "good" and "bad" electrode and circuitry dies can also be identified using other inspection methods. For at least cost-effective purposes, a semiconductor wafer having a suitable number and distribution of the "bad" and "good" electrode and circuitry dies is preferably selected for matching a given glass wafer so as to statistically optimize the production yield, as set forth in U.S. patent application "Wafer Matching Method for Use in Assembling Micromirror Array Devices", 10/875,987, filed on the same day as the current patent application, the subject matter being incorporated herein by reference. The selected semiconductor wafer having the electrode and circuitry dies is then assembled with the glass wafer; and broken into assembled dies. The assembled dies may receive further treatments, such as surface treatments or can be packaged for delivery to customers.

In accordance with the inspection method of the invention, an apparatus for performing the inspection and analysis is further provided. The apparatus comprises a light source providing collimated light for illuminating the reflective deflectable elements on the wafer, and an image capture device for capturing reflected light from the deflectable elements. Due to the small dimension of the deflectable elements and larger cross-section of the incident light beam, a plurality of the elements on the wafer is illuminated at a time. A photodetector is disposed in the propagation path of the reflected light from the deflectable elements for collecting such reflected light, and transforms the intensity of the collected light into electrical signals. The transformed electrical signals are then delivered to a network analyzer and analyzed along with the AC voltage signals provided by the analyzer for oscillating the deflectable elements.

In operation, the analyzer sweeps the frequency of the AC voltage for a number of deflectable elements on the wafer. When the frequency of the AC voltage is approximately the intrinsic resonance frequencies of the number of deflectable elements, the intensity of the reflected light is maximized. Accordingly, the network analyzer detects a peak around the resonance frequency in the signal intensity vs. frequency plot. The resonance frequencies of the deflectable elements across the entire wafer are measured. Due to the variations of the deflectable elements (and/or the deformable elements whose properties determine the movements of the deflectable elements) in deflections and/or geographic configurations, the resonance frequencies of these elements exhibit a distribution across the wafer. Uniformity information of the elements on the wafer can thus be extracted from the frequency distribution, and quantitatively or qualitatively analyzed.

The inspection method and system of the present invention is simple, fast, reliable, compact, and allows for easy identification and documentation of wafer assembly or die assembly defects. The inspection system can comprise one or more light sources, a diffuser, a narrow band filter, collimating lens, steering mirrors, detectors, imaging optics, CCD camera and control monitor or screen. The inspection system allows defect detection for an entire wafer surface in a single field of view, thus reducing inspection time.

The present invention is applicable to microelectromechanical devices having deflectable reflective planar members that requiring uniformity after releasing. For simplicity and demonstration purposes only, the present invention will be discussed with reference to spatial light modulators having micromirrors, each of which has a deflectable reflective mirror plate that is supported by a deformable hinge.

Referring to the drawings, FIG. 1 illustrates a perspective view of wafer 100 having a plurality of dies after removal of the sacrificial material. Each die may have thousands or millions of micromirror devices arranged into a micromirror array. For example, each die may have an array of micromirrors, wherein the array may have 1024×768 or more, or 1280×1024 or more, or 1640×1280 or more micromirrors.

Each die can be a fully developed spatial light modulator or a portion of a spatial light modulator. As an example, the micromirror array can be formed on a semiconductor substrate that further comprises an array of electrodes and circuitry for addressing and deflecting the mirror plates of the micromirror array. In this situation, each die can be a spatial light modulator. Alternatively, the wafer can be a light transmissive wafer such as glass; and each die comprises an array of micromirrors. After fabrication, each die will be assembled with another die having the electrodes and circuitry for addressing and actuating the micromirrors. In the following, the present invention will be discussed with examples in which the wafer is a glass substrate that comprises a plurality of dies, each of which further comprises an array of mirror plates with each mirror plate being attached to a hinge.

Figure 2:
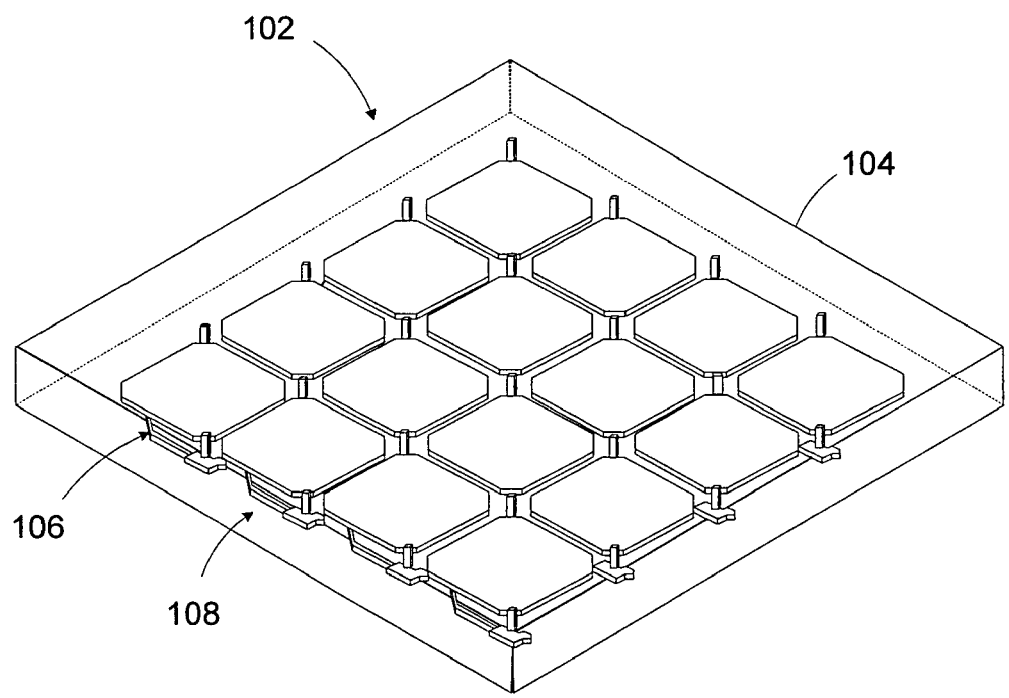
FIG. 2 is a perspective view of a die having an array of micromirrors after removal of the sacrificial material.

FIG. 2 is a perspective view of a portion of a die in FIG. 1. In this particular example, the die comprises an array of micromirrors 106 formed on glass substrate 104. Each micromirror operates in a binary-mode, that is, the micromirror switches between an ON state and OFF state in operation (though analog devices can also be tested). In the ON state, the micromirror reflects incident light so as to generate a "bright" pixel on a display target; and in the OFF state, the micromirror reflects the incident light so as to generate a "dark" pixel on the display target. In a number of possible embodiments of the invention, the micromirror array is constructed to have a pitch (the center-to-center distance between adjacent micromirrors) of 50 micrometers or less, or from 4 to 20 micrometers. The gap between adjacent micromirrors is approximately of 5 micrometers or less, or from 0.1 to 2 micrometer. And the mirror plate of the micromirror has a dimension of from 10 micrometers to 20 micrometers. The mirror plates of the micromirror array are held below the glass substrate by hinges such that the mirror plates can rotate relative to the glass substrate. The mirror plates as show in the figure are substantially square; and the hinges are hidden under the mirror plates. This configuration, however, is one example. Instead, the mirror plate can take any desired shapes; and the hinge cane be formed at any suitable relative positions to the mirror plates and the substrate as long as the mirror plates can rotate relative to the glass substrate.

The micromirrors can be formed in a variety of ways. Regardless the difference, a sacrificial material is used in forming the functional members of the micromirror devices. As a way of example, the micromirror array as shown in FIG. 2 can be formed as follows. With prepared glass substrate 104, a sacrificial layer having selected sacrificial material, such as amorphous silicon is deposited on the glass substrate. A mirror plate layer is then deposited and patterned for forming the mirror plate array. Then another sacrificial layer is deposited and patterned for forming other functional members, such as hinges and posts of the micromirror array. On the patterned sacrificial layer(s), the hinges and posts can be formed but not necessarily in that order. Based on the particular design of the micromirror array, other sacrificial layers may be deposited as appropriate.

After completion of the desired functional members of the micromirrors, the sacrificial material is removed using one or more suitable method, such as a spontaneous vapor phase chemical etching with a selected vapor phase chemical etchant(s), such as xenon difluoride.

After removal of the sacrificial material, the mirror plates of the micromirror array are free to rotate relative to the glass wafer. The rotation of each mirror plate is determined by many factors, such as the geometric configuration (e.g. length, width and thickness) of the hinge, mechanical properties of the hinge (e.g. the shear modulus of hinge which is further determined by the material of the hinge), and the external torque causing the rotation of the mirror plate that is attached to the hinge. On the other hand, these factors characterize the uniformity of the micromirrors on glass wafer. Therefore, uniformity information of the micromirrors can be extracted from the rotation behaviors of the mirror plates.

THEORY RELATED TO THE INVENTION

The mechanical movement of the mirror plate with a disturbing driving force can be modeled as a harmonic oscillator. Particularly, in the absence of air dumping, a small perturbing AC voltage as compared to the voltage necessary for rotating the mirror plate to an operation state (e.g. the ON state) can drive the mirror plate to oscillate in the vicinity of its natural resting state (e.g. the OFF state). When the frequency f of the AC voltage applied to the mirror plate substantially the intrinsic resonance frequency $f_0$ of the mirror plate, the oscillation is maximized, as expressed in equation 1.

$$f = f_0 = \frac{1}{2\pi}\left[\frac{1}{I}\left[k_H - \frac{\partial \tau_E}{\partial \theta}(V = V_0, \theta = \theta(V_0))\right]\right]^{\frac{1}{2}} \quad \text{Eq. 1}$$

wherein I is the oscillation inertia; $\tau_E$ is the torque of the external force such as electrostatic force at an applied DC bias $V_0$; V is the amplitude of the voltage applied to the mirror plate. $K_H$ is the spring constant determined by the hinge, which can be written as:

$$K_H = K_0 \frac{\gamma \cdot w \cdot t^3}{l} \quad \text{Eq. 2}$$

wherein $K_0$ is a constant; $\gamma$ is the shear modulus of the hinge; w is the width of the hinge; t is the thickness of the hinge; and l is the length of the hinge. It can be seen from equations 1 and 2 that the resonance frequency depends upon hinge stiffness (represented by the shear modulus $\gamma$) angular polar momentum, and angle-derivative of the electrostatic torque at the DC component of the voltage applied to the mirror plate and at the equilibrium angle. The derivative term in equation 1 is a manifestation of the non-linear nature of the mechanical rotation of the mirror plate.

When the voltage applied to the mirror plate does not have DC component, and the amplitude of the AC component is a small disturbance as compared to the voltage necessary for rotating the mirror plate to an operation state (e.g. ON state), the resonance frequency $f_0$ is a function solely of the mirror plate's parameters—hinge stiffness and polar moment. Specifically, $K_H$ and I can be disentangled if the resonance frequency dependence on the applied DC component is measure in the non-linear regime. However, a simplified $f_0$ as expressed in equation 3 is a satisfactory measure of the hinge stiffness, and can thus be use to characterize the uniformity of the micromirrors on the wafer, which can be affected by many factors, such as over-etching during the removal process of the sacrificial materials; and/or by lesser extent in film deposition variances across the entire wafer.

$$f = f_0 = \frac{1}{2\pi}\sqrt{\frac{K_H}{I}} \quad \text{Eq. 3}$$

Experimental Setup and Measurements

Figure 3A:
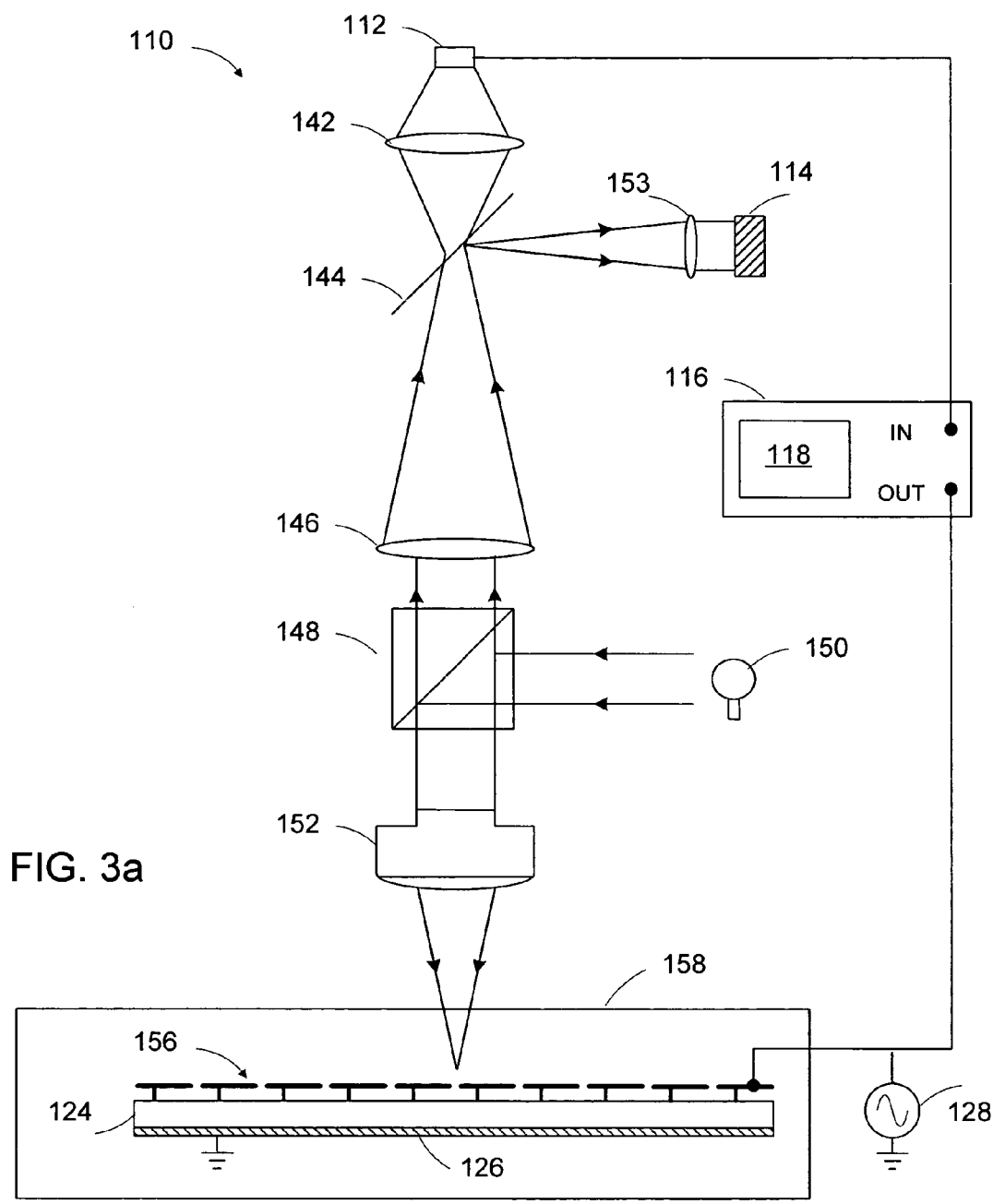
FIG. 3a illustrates an exemplary setup for measuring resonance frequencies of the micromirrors on a wafer.
Figure 3B:
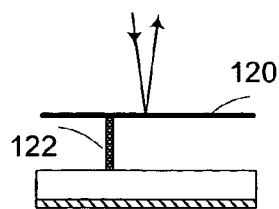
FIG. 3b demonstratively illustrates a micromirror at a non-deflected state.
Figure 3C:
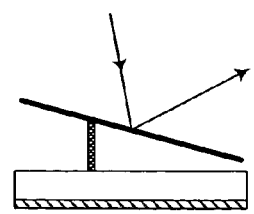
FIG. 3c demonstratively illustrates a micromirror at a deflected state.

FIG. 3a is a simplified experimental setup for inspecting the uniformity of the micromirrors after removal of sacrificial materials on a glass wafer according to an embodiment of the invention. For demonstration and simplicity purposes without losing the generality, an exploded view of a portion of the micromirrors on the wafer are illustrated in a cross-sectional view. In particular, a micromirror in a non-deflected state is illustrated in FIG. 3b. Referring to FIG. 3b, the micromirror comprises deflectable reflective mirror plate 120 and deformable hinge 122 with the mirror plate attached thereto such that the mirror plate can rotate relative to the glass substrate.

Turning back to FIG. 3a, the experimental setup 110 comprises an objective 152, a light source 150, a beam-splitting cube or plate 148, a tube lens 146 that images the micromirror array onto a pinhole in the mirror 144, a relay lens assembly 153 that relays the image of micromirrors onto a camera sensor 114. The light source can be a white bulb, a laser, LED or any suitable light emitting devices. The light reflected by mirrors imaged onto a pinhole in the mirror 144 gets focused by lens 142 onto a fast photodetector 112. A micromirror wafer 124 rests on a conducting plate 126 inside a vacuum chamber 158. A reference AC signal of the network analyzer 116 is applied between released micromirrors 156 and a conducting plate 126. Frequency dependence of the rms voltage output of the photodetector 112 which is proportional to the intensity of collected light is measured by the network analyzer 116. The experiment setup may also have a sample holder for holding the micromirror array device. The sample holder can positioned within the vacuum chamber if the micromirror array device is to be measured in vacuum. The sample holder can be a flat surface on which the micromirror array device is attached. The sample holder may have a supporting surface for supporting and holding the micromirror array device. The supporting surface is preferably movable. For example, the supporting surface can move in horizontally and vertically, and more preferably can tilt at any desired angles, such that the reflecting surface of the micromirror array device can be tilted to any desired angles. As a result, the reflected light from the reflecting surface of the micromirror array device can be directed towards any desired directions. Moreover, the sample holder can be equipped with an automation system, such as a motor, as well as a position detector. In this way, movements the sample holder can be automated, and the position of the sample holder can be measured precisely.

In accordance with an embodiment of the invention, the components of the system in FIG. 3a are arranged according to the configuration of the device to be measured. For example, when a micromirror array device having an array of deflectable reflective mirror plates is to be measured, the image capture device is desired to be positioned in the propagation path of the reflected light when the mirror plates are at a particular state. For example, mirror plate can rotate to an ON state angle and an OFF state angle, or not rotated (e.g. parallel to the substrate on which the micromirror is formed). The image capture device can thus be positioned in the propagation path of the reflected light from the mirror plate at the ON state angle, the OFF state angle or parallel to the substrate. When the image capture device is positioned in the propagation path of the reflected light from the mirror plate at the ON state, the detected illumination intensity of the reflected light will increase as the mirror plate rotates towards the ON state angle. When the photodetector is positioned in the propagation path of the reflected light from the mirror plate parallel to the substrate, the detected illumination intensity decreases as the mirror plate rotates towards the ON state angle. As a way of example, the image capture device can be positioned at a location wherein an imaginary line connecting the device to be measure has an angle to the incident illumination light, wherein the angle can be 0° degree, 10° degrees or more, 12° degrees or more, 14° degrees or more, 16° degrees or more, 18° degrees or more, 20° degrees or more, and 22° degrees or more.

In a measurement, the vacuum chamber is pumped out to a pressure below 1 Torr, such as 200 mTorr or less, or 100 mTorr or less so as to minimize air damping. A perturbing AC voltage is applied between the mirror plates and the conducting plate. The AC voltage has small amplitude as compared to the voltage necessary for rotating the mirror plate to an operation state (e.g. the ON state). In accordance with the examples of the invention, the AC voltage has an amplitude that is 10% or less, or 10% or less, or 0.1% or less of the amplitude of the voltage necessary for rotating the mirror plate to the ON state of the mirror plate. The induced oscillation is preferably between ±0.1% or less, or 10% or less, or 30% or less of the ON state angle that can be 8° degrees or more, or 10° degrees or more, or 12° degrees or more, or 14° degrees or more depending upon the particular configuration of the micromirror. As a way of example, the voltage necessary for rotating the mirror plate to the ON state by an electrode (not shown) in operation is 50V. The amplitude of the AC voltage can be around 1V. The corresponding electric field in the air gap between the glass wafer and the mirror plate is approximately 71 V/mm for 700 microns-thick glass wafer. Driven by the AC voltage, the mirror plate oscillates in the vicinity of its equilibrium state (e.g. its natural resting state). The oscillation amplitude is small as compared to the rotation angle corresponding to the ON state.

For measuring frequency response of mirror plates, a preferably collimated white light from source 150 and reflected by a beam splitter 148 illuminates micromirrors 156 on a substrate 124. Mirrors reflect the light which passes through the objective, the beam splitter 148, the tube lens 146, and pinhole in the mirror 144, and finally get collected by focusing lens 142 on a photodetector 112. When mirrors are rotated away from their horizontal rest state, as shown in FIG. 3b, the light intensity measured by a photodetector 112 is smaller than that in the case of mirrors at rest. Therefore, mirror rotation modulates the photodetector response measured by the network analyzer 116. The objective magnification determines the number of micromirrors imaged onto a pinhole in the mirror 144, and, consequently, the number of mirrors averaged into the frequency response. A plurality of objectives may be mounted on a turret, thereby allowing mirror response measurements averaged over different sized mirror arrays. In one possible implementation, the objective 152 is an infinity corrected objective with 20× magnification, and the tube lens has a focal length of 200 mm. The micromirror is 10 um on a side, and the pinhole in mirror 144 is 400 um wide. In this configuration, frequency response measured is averaged over 4 mirrors. If a 2× infinity-corrected objective is used instead, frequency response is averaged over 400 mirrors. According to an embodiment of the invention, the illumination light beam is preferably adjusted such that 100 or less, or 500 or less, or 1000 or less micromirrors can be illuminated at a time. According to yet another embodiment of the invention, the illumination light can be adjusted such that 1000 or more micromirrors are illuminated at a time.

Figure 4:
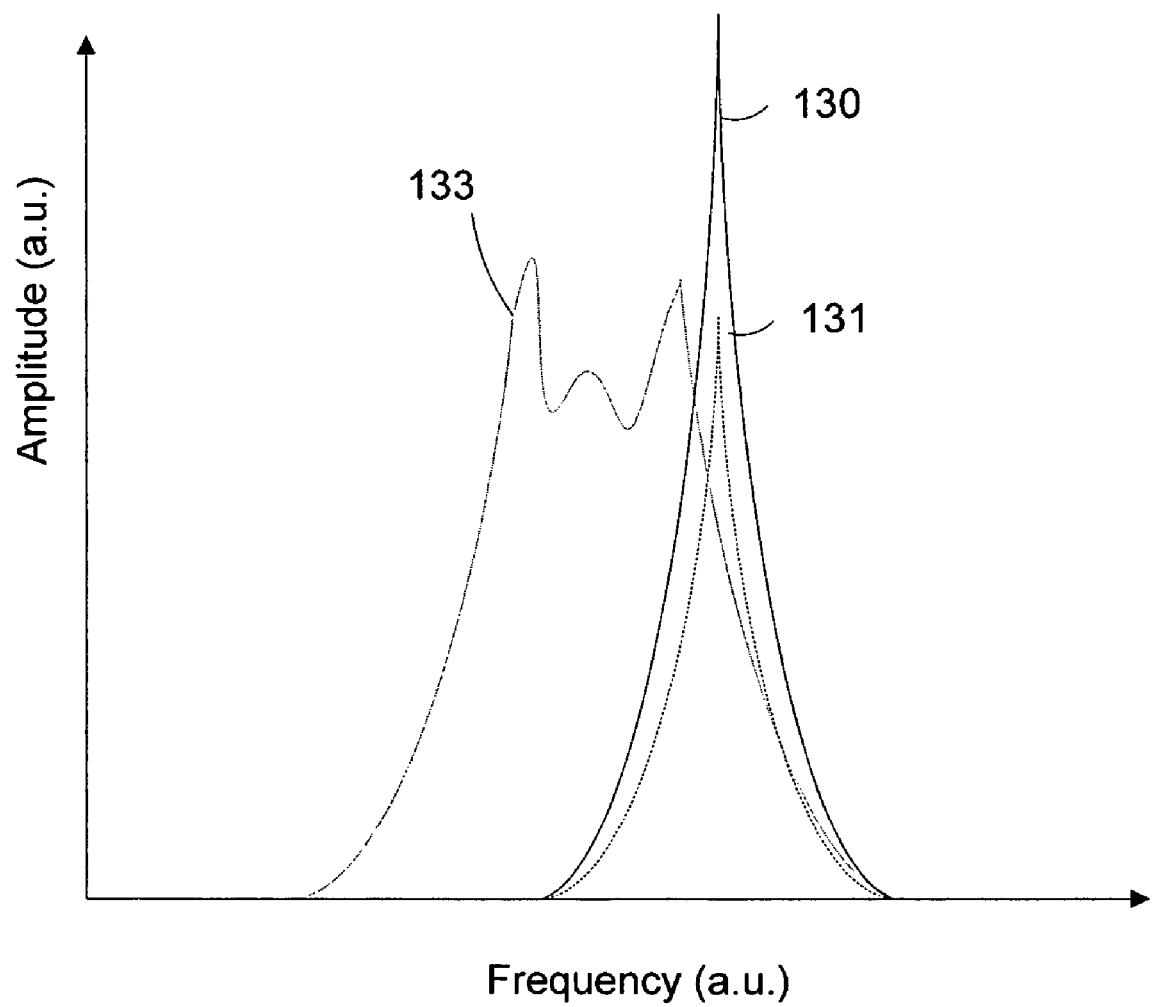
FIG. 4 diagrammatically illustrates resonance profiles of micromirrors with different uniformities.

The network analyzer sweeps the frequency of the AC voltage during a single scan. When the frequency of the AC voltage is approximately the intrinsic resonance frequency of the mirror plates, the oscillation the mirror plate is maximized, so as to modulate the intensity of the reflected light from the mirror plate and into the photodiode. The resonance is characterized by a peak in the signal amplitude vs. frequency plot, as shown in FIG. 4.

Because a number of micromirrors are actuated and measured at a time, the shape of the frequency response also depends upon the resonance distribution of all mirror plates being illuminated and measured, in addition to the response of individual micromirrors, which depends upon mechanical properties of the micromirrors and other factors, such as air damping. That is, the measured resonance is a cumulative frequency response of a group of mirror plates. For quantitatively characterizing the resonances from the mirror plates being detected, an average peak frequency f as defined in equation 3 and a quality-of-peak Q are extracted from the accumulated resonance response. The quality-of-peak Q can be quantitatively described by a mathematic function of full-width-half-maximum (FWHM) of the frequency responses. The FWHM of the frequency response takes the ratio of the signal integrated over the frequency scan range to the peak value, as expressed in equation 4.

$$Q = \frac{f_0}{\Delta f} = f_0 I(f_0) \bigg/ \int I(f) df \qquad \text{Eq. 4}$$

Because the oscillations of more than one mirror plates (e.g. from 10 to 100 micromirrors, or from 100 to 500 micromirrors, or from 500 to 1000 micromirrors, or 1000 to 2000 micromirrors, or 2000 or more micromirrors illuminated by the incident light beam) are measured at a time, the profile of the intensity vs. frequency curve is in fact a summation of the intensity vs. frequency curve of a single mirror plate; and the function in equation 4 describes the local distribution of the resonance frequencies. For this reason, Q as defined in equation 4 measures the local uniformity of the mirror plates illuminated by the incident light at the time. When all micromirrors are identical, the resonance frequencies of the individual mirror plates are the same, and Q measures the damping of the mirror plates.

FIG. 4 plots different distributions of resonance frequencies of wafers having different levels of uniformity. Profiles 131 and 132 are obtained from the same wafer but measured at different chamber pressures with the measurement parameters otherwise kept the same. Specifically, curve 130 is measured at a lower pressure (i.e. 500 mTorr) than the pressure (i.e. 5 Torr) at which curve 131 is measured. Obviously, curve 130 has a much sharper peak than curve 131. This arises from the fact that the damping of the mirror plate is depressed in lower pressure (higher vacuum level). Therefore, the resonance frequency is preferably measured in a low pressure, or equivalently, a high vacuum level.

Curve 133 plots the intensity vs. frequency from a wafer having a poor uniformity than the wafer in curves 130 and 131, but is measured at the same pressure (or vacuum level) as curve 130. It can be seen that curve 133 is widely spread out in frequencies; and the resonance peak is smeared because of the poor uniformity of the micromirrors on the wafer.

In order to obtain the resonance frequencies of all mirror plates across the entire wafer so as to extract uniformity information thereof, the measurement setup 110 scans the mirror plates across the wafer. At a time, the incident light beam illuminates a plurality of mirror plates at a location on the wafer and stays for a time period for allowing the network analyzer to scan the frequency of the applied AC voltage to the mirror plates at the location so as to obtain a resonance frequency. After obtaining the resonance frequency of the mirror plates at the location, the measurement setup 110 moves by a predetermined step to the next location, and the resonance frequency is measured. The process continues until the entire wafer is scanned; and the resonance frequencies thereof are measured.

The distribution of the resonance frequencies of the mirror plates on the wafer can then be analyzed to extract the uniformity information, which will be demonstratively discussed in the following with reference to FIGS. 5 through 8b.

Figure 5:
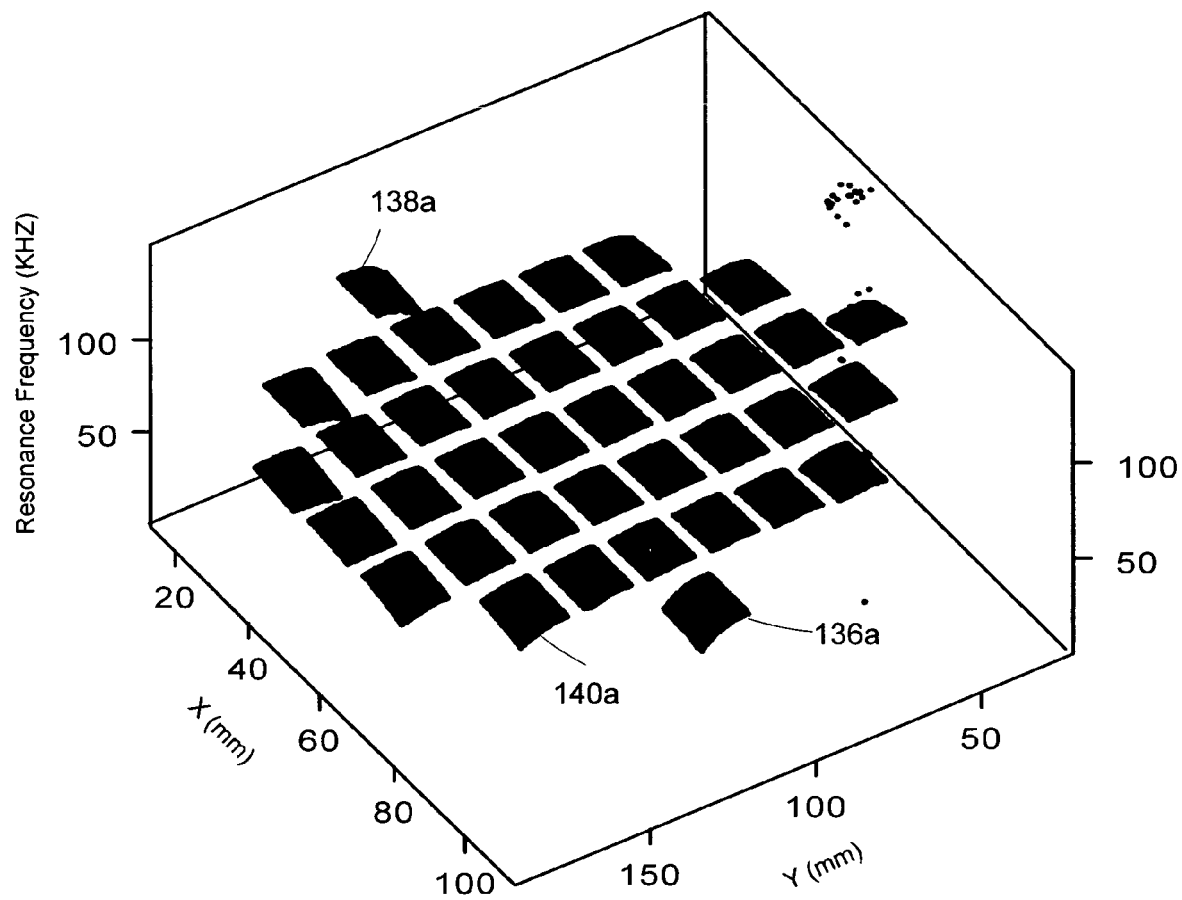
FIG. 5 is a surface plot of resonance frequencies of the micromirrors on a wafer.

Referring to FIG. 5, a surface profile of the resonance frequencies at different locations of a wafer that has a high uniformity. Z-axis plots the resonance frequency. X-axis plots the x-coordinates of the mirror plates on the wafer; and Y-axis plots the y-coordinates of the mirror plates on the wafer. It can be seen from the figure that, the variation of the resonance frequency is around 1% or less across the frequency surface, which can be better seen in FIGS. 6a and 6b. The surface profile is an "image" of the dies as shown in FIG. 1. The small variation of the resonance frequencies of the mirror plates and the sharp "image" of the dies on the wafer indicate a satisfactory uniformity of the mirror plates on the wafer. More uniformity information can be extracted from the resonance frequency surface profile. For example, frequency "blocks" 136a, 138a, and 140a correspond to the dies 136, 138, and 140 in FIG. 1, respectively. These frequency "blocks" have a higher frequency variation than the average (i.e. 1%). It indicates that the dies 136, 138, and 140 each have a lower uniformity than the remaining dies on the wafer. These dies can be marked as "bad" dies if their frequency variations are beyond the predetermined threshold, such as 1%. The location(s) of the "bad" die(s) can be saved for further usage. For example, during the assembly process, a semiconductor wafer having the electrode and circuitry dies thereon is selected according to the locations of the "bad' dies in the glass wafer so as to maximize the production yield. After such wafer-level assembly, the assembled "bad" dies will be discarded after assembly.

Figure 6A:
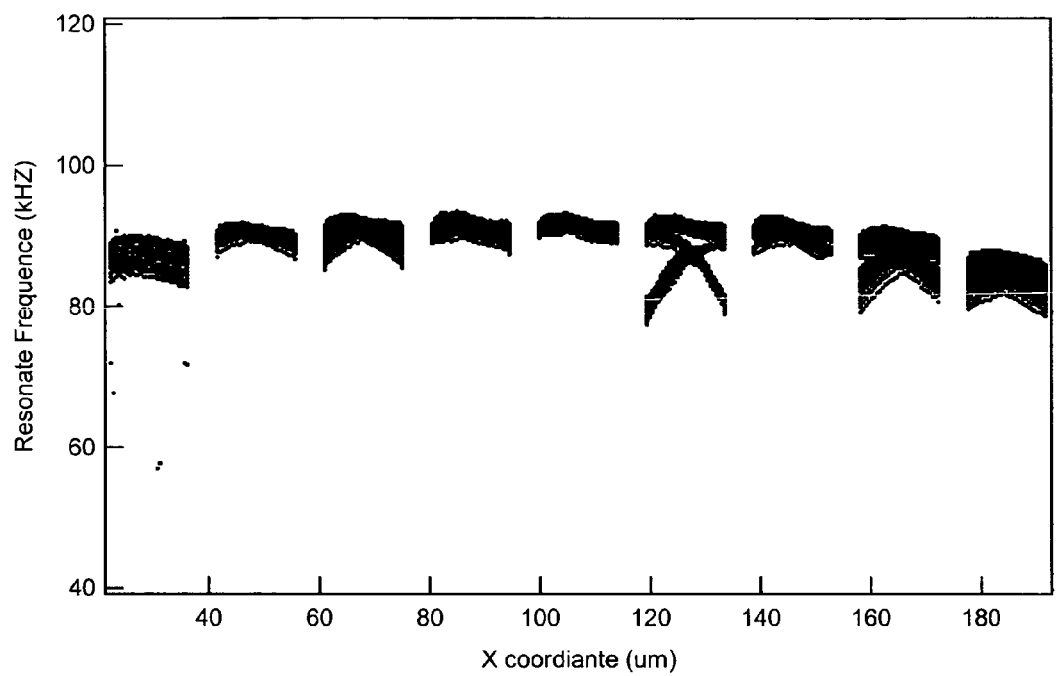
FIG. 6a plots the projection of the surface plot in FIG. 5 in the frequency-X coordinate plane.
Figure 6B:
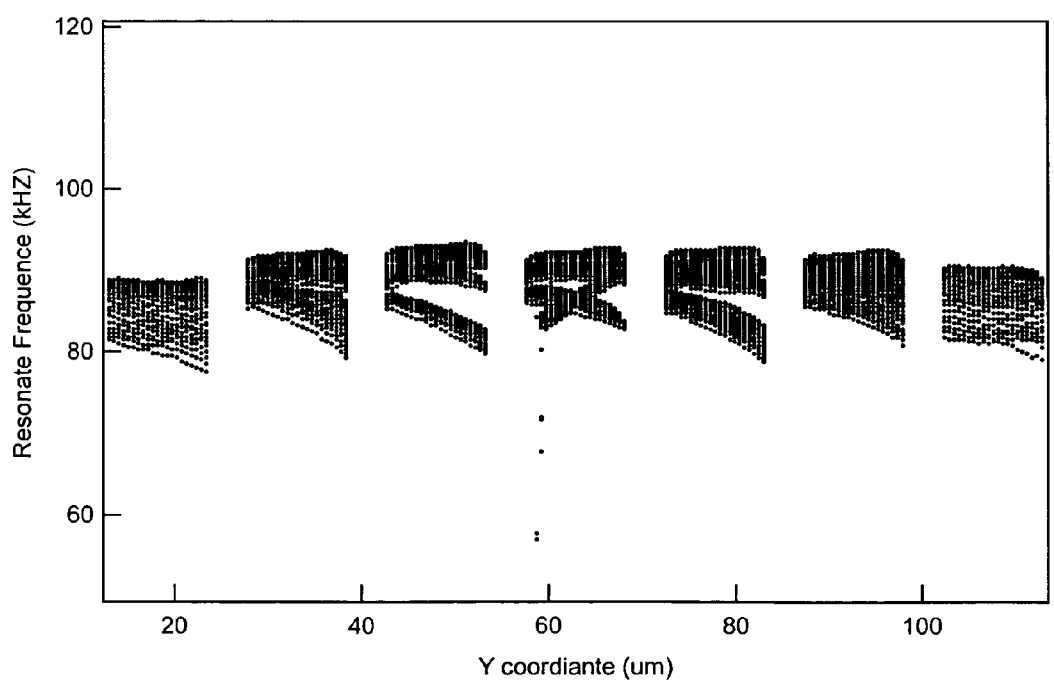
FIG. 6b plots the projection of the surface plot in FIG. 5 in the frequency-Y coordinate plane.

FIGS. 6a and 6b respectively plot the projections of the surface profile in FIG. 5 in the x-axis and frequency plane, and the y-axis and frequency plane. It can be seen from the plots that the variation of the resonance frequency in the x-axis is averaged around 1%, while the variation of the resonance frequency in the y-axis is averaged around 1.7%.

Figure 7:
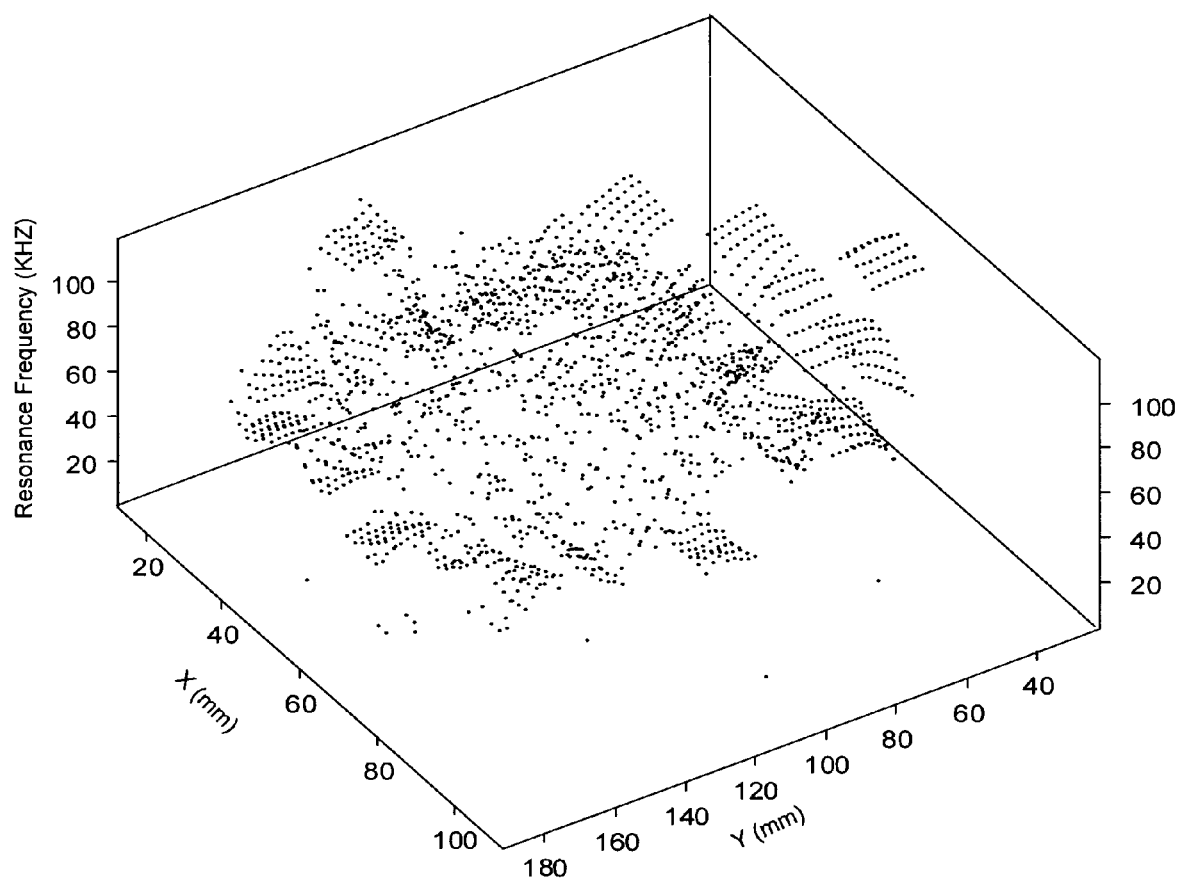
FIG. 7 is another surface plot of resonance frequencies of the micromirrors on a wafer.
Figure 8A:
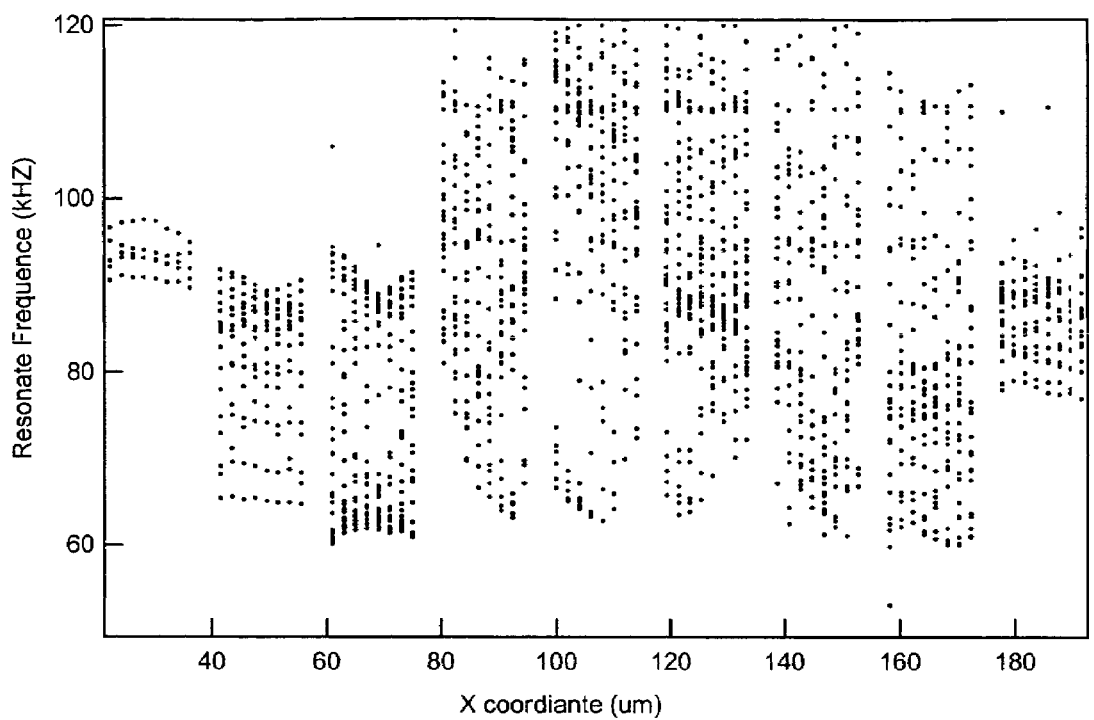
FIG. 8a plots the projection of the surface plot in FIG. 7 in the frequency-X coordinate plane.
Figure 8B:
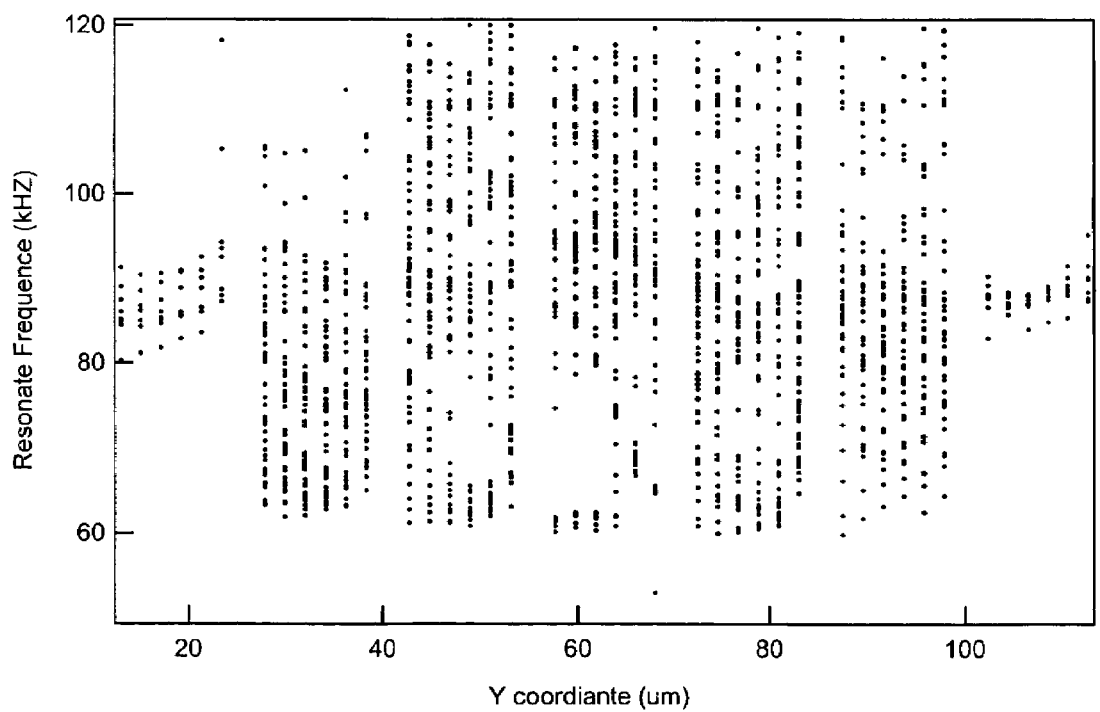
FIG. 8b plots the projection of the surface plot in FIG. 7 in the frequency-Y coordinate plane.

As a comparison, FIG. 7 presents a surface profile of the resonance frequencies at different locations of another wafer that has a lower uniformity than the uniformity of the wafer in FIG. 5. It can be seen from the figure that the resonance frequencies of the mirror plates on the wafer is spread out, and the variation of the resonance frequency is more than 50%, which can be better seen in FIGS. 8a and 8b. There is no discernable correspondence of resonance frequency "blocks" to the dies on the wafer. If the predetermined threshold of the resonance frequency variation for evaluating the quality of the dies is 1% or less, the dies on the wafer are marked as "bad". FIGS. 8a and 8b respectively plot the projections of the surface profile in FIG. 7 in the x-axis and frequency plane, and the y-axis and frequency plane. It can be seen from the plots that the variation of the resonance frequency in the x-axis and y-axis are averaged more than 50%.

Based upon the extracted quantitative information (e.g. the variation) of the resonance frequency distribution, the product quality can be evaluated with a predetermined criterion. For example, a die on a wafer having a variation of the resonance frequency equal to or below the threshold (e.g. 10% or less, or 5% or less, or 1% or less, or 0.5% or less) can be accepted as a "good" die; while a die having the variation otherwise can be marked as a "bad" die. The location information of the "good" and "bad" dies can then be used in the future processes or quality assurance.

As discussed above, the frequency resonances of the micromirrors are measured so as to evaluate the uniformity of the micromirrors. In particular, AC voltages are applied to the mirror plates each of which oscillates in the vicinity of an equilibrium state—a state where the mirror plate is parallel to the substrate. This method can be extended to measure the material parameters of the micromirrors, such as the mechanical properties of the hinge. For this purposes, the measurement can be performed in a torsional mode or a hinge-lifted mode. In the torsional mode, the mirror plate and the hinge are in natural resting state, while in the hinge-lifted state, the mirror plate is deflected and the hinge is deformed.

Figure 9A:
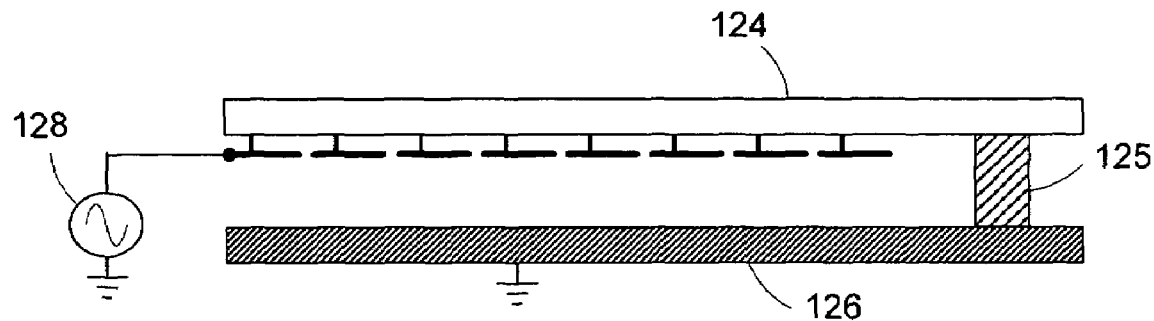
FIG. 9a illustrates another experimental set up for measuring resonance frequencies of the micromirrors on a wafer.

According another embodiment of the invention, the frequency resonance of the micromirrors can be measured in an experimental setup as illustrated in FIG. 9a. Referring to FIG. 9a, conducting plate 126 is placed on the same side of substrate 124 (which in this case is light transmissive) but at a distance from the mirror plate. The distance is controlled by spacer 125. In this particular experimental setup, the conductor plate is grounded, and the perturbing voltage $V_{AC}$ is applied between the mirror plates and the conducting plate. Measurement methods and data analyses used in the experiment setup in FIG. 3a can also be employed herein.

Figure 9B:
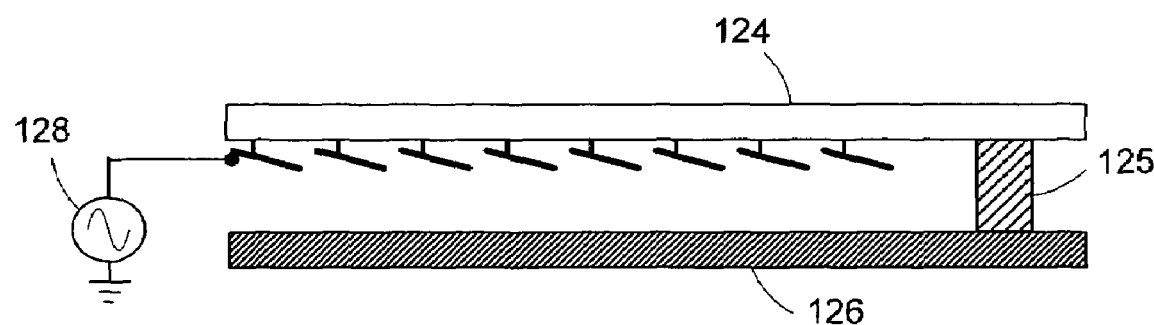
FIG. 9b illustrates yet another experimental set up for measuring resonance frequencies of the micromirrors on a wafer.

According to yet another embodiment of the invention, frequency resonance of the micromirrors can be measured in the ON state, as shown in FIG. 9b. A DC voltage is applied to the conducting plate. With the DC voltage, the micromirrors are rotated to the ON state. The AC voltage is applied between the mirror plates and the conducting plate resulting in oscillations of the mirror plate in the vicinity of their ON states. In this configuration, the resonance of the micromirrors is defined by equation 1. The second term $$\frac{\partial \tau_E}{\partial \theta}(V = V_0, \theta = \theta(V_0))$$

of equation 1 provides information on the uniformity of the micromirrors at the ON state. This is especially useful when the micromirrors have different uniformities at their natural resting (e.g. OFF) state and the ON state.

It will be appreciated by those of skill in the art that a new and useful method and system for qualitatively evaluating product quality of microelectromechanical devices have been described herein. In view of the many possible embodiments to which the principles of this invention may be applied, however, it should be recognized that the embodiments described herein with respect to the drawing figures are meant to be illustrative only and should not be taken as limiting the scope of invention. For example, those of skill in the art will recognize that the illustrated embodiments can be modified in arrangement and detail without departing from the spirit of the invention. In particular, the present invention is also applicable to other types of micromirror array devices. For example, the present invention is applicable to a micromirror device wherein the micromirror substrate is formed on a transfer substrate that is light transmissive. Specifically, the micromirror plate can be formed on the transfer substrate and then the micromirror substrate along with the transfer substrate is attached to another substrate such as a light transmissive substrate followed by removal of the transfer substrate and patterning of the micromirror substrate to form the micromirror. Alternatively, the present invention is applicable to a micromirror array device wherein the micromirror array is formed on the same substrate as the electrode and circuitry, in which situation, the metallic plate (e.g. metallic plate 126 in FIG. 3a) is not be required. Moreover, the metallic plate provide for the driving voltages (e.g. metallic plate 126 in FIG. 3a) may be composed of metallic segments, each of which behaves like an electrode associated with a mirror plate of a micromirror. The driving voltages can then be applied between the electrodes and the mirror plates of the micromirrors. Therefore, the invention as described herein contemplates such embodiments as may come within the scope of the following claims and equivalents thereof.

We claim:

1. A method of evaluating a quality of a plurality of microelectromechanical devices on a wafer, each microelectromechanical device having a reflective and deflectable plate attached to a deformable hinge that is held on the wafer; the method comprising:
    measuring a distribution of a resonant frequency of the microelectromechanical device comprising:
    illuminating a number of the reflective and deflectable plates with a light beam;
    applying an AC voltage to the number of plates such that the plates oscillate in vicinity of their equilibrium states; and
    sweeping the frequency of the AC voltage, and measuring the frequency response of the reflected light beam from the illuminated plates; and
    evaluating and displaying said quality of a uniformity of the microelectromechanical device on the wafer based on the measured distribution of the resonant frequency.

2. The method of claim 1, wherein the microelectromechanical device is a micromirror array device having an array of micromirrors.

3. The method of claim 2, wherein the step of measuring the distribution of the resonant frequency further comprises:
    measuring the resonant frequency from a number of micromirrors at a time;
    repeating the measurement for the micromirrors across the wafer; and
    obtaining the distribution based on the measured resonant frequencies of the micromirrors across the wafer.

4. The method of claim 2, wherein the number of micromirrors is 100 or less.

5. The method of claim 2, wherein the number of micromirrors is from 500 to 5000.

6. The method of claim 2, wherein the number of micromirrors is 1000 or more.

7. The method of claim 2, wherein each of the plurality of the mirror plates on the wafer has a dimension of 50 microns or less.

8. The method of claim 2, wherein each of the plurality of the mirror plates on the wafer has a dimension of 20 microns or less.

9. The method of claim 2, wherein the plurality of the mirror plates on the wafer is organized into a set of mirror plate arrays, wherein the adjacent mirror plates within an array have a center-to-center distance of 20 microns or less.

10. The method of claim 2, wherein the step of evaluating the quality of the mirror plates further comprises:
    calculating a variation of the resonance frequencies of the mirror plate across the wafer; and
    evaluating the quality of the mirror plates based on the calculated variation.

11. The method of claim 10, further comprising:
    marking a die on the wafer as "good" if the variation of the resonance frequency of the die is equal to or less than the predetermined quality criterion.

12. The method of claim 11, wherein the predetermined criterion is that the variation of the resonance frequency is 2% or less.

13. The method of claim 11, wherein the predetermined criterion is that the variation of the resonance frequency is 1% or less.

14. The method of claim 2, further comprising:
placing the wafer having the mirror plates and hinges into a chamber that has a pressure of lower than 1Torr.

15. The method of claim 14, wherein the pressure inside the chamber is 200 mTorr or less.

16. The method of claim 14, wherein the pressure inside the chamber is 100 mTorr or less.

17. The method of claim 14, wherein the wafer is light transmissive.

18. The method of claim 17, wherein the light transmissive wafer is glass.

19. The method of claim 2, wherein the steps are performed in the absence of a semiconductor wafer having a plurality of electrodes and circuitry formed thereon.

20. The method of claim 2, wherein the step of determining the uniformity further comprises:
passing the microelectromechanical device if the uniformity is within a predetermined threshold; and
failing the microelectromechanical device if the uniformity is beyond the predetermined threshold.

21. The method of claim 1, wherein the parameter is measured in the absence of a DC voltage.

22. The method of claim 1, wherein the AC voltage has an amplitude that is 10% or less of a voltage amplitude necessary for rotating the mirror plate to an ON state that corresponds to a rotation angle of 12° degrees or more.

23. The method of claim 13, wherein the amplitude of the AC voltage is 1% or less of the amplitude of the voltage necessary for rotating the mirror plate to the ON state.

24. The method of claim 1, further comprising:
measuring the uniformity with a quality-peak Q that is a function of the full-width-half-maximum (FWHM) of the frequency response, wherein the FWHM is defined as a ratio of the frequency integrated over the frequency scan range to the peak value of the frequency resonance peak.

25. The method of claim 11, further comprising:
detecting a light beam reflected from the mirror plates, wherein the reflected light propagates along a direction that is perpendicular to a surface of the plates of the microelectromechanical devices when the plates are at a natural resting state.

26. A method of evaluating a quality of a plurality of microelectromechanical devices on a wafer, each microelectromechanical device having a reflective and deflectable plate attached, the method comprising:
applying an AC voltage in the absence of a DC voltage to a plurality of the plates to cause each of the plurality of plates to resonate in the vicinity of an equilibrium state;
detecting a resonate frequency of the plate; and
determining and displaying the quality of themicroelectromechanical device based upon the detected resonance frequency.

27. The method of claim 26, wherein the step of determining the quality further comprises:
passing the microelectromechanical device if the detected resonance frequency is within a predetermined threshold; and
failing the microelectromechanical device if the detected resonance frequency is beyond the predetermined threshold.

28. A method of evaluating a quality of a plurality of microelectromechanical devices on a wafer, each microelectromechanical device having a reflective and deflectable plate attached, the method comprising:
moving a plurality of plates of the microelectromechanical devices to a particular state with a DC voltage;
applying an AC voltage to the plurality of plates to cause each of the plurality of plates to resonate in the vicinity of an equilibrium position of the particular state;
detecting a resonate frequency of the plate; and
determining and displaying the quality of the microelectromechanical device based upon the detected resonance frequency;
wherein in the particular position, the plate has an angle to a substrate on which the plates are formed; and
wherein the angle is 14° degrees or more.

29. The method of claim 28, wherein the step of determining the quality further comprises:
passing the microelectromechanical device if the detected resonance frequency is within a predetermined threshold; and
failing the microelectromechanical device if the detected resonance frequency is beyond the predetermined threshold.

30. The method of claim 28, wherein the angle is 18° degrees or more.

31. The method of claim 28, wherein the angle is 20° degrees or more.

32. The method of claim 28, wherein the angle is 22° degrees or more.

* * * * *